United States Patent
Wermuth

(10) Patent No.: US 7,514,454 B2
(45) Date of Patent: Apr. 7, 2009

(54) PIPERIDIN-2,6-DIONE PAMOATE SALTS AND THEIR USE FOR THE TREATMENT OF STRESS-RELATED AFFECTIVE DISORDERS

(75) Inventor: Camille Georges Wermuth, Illkirch (FR)

(73) Assignee: Prestwick Pharmaceuticals, Inc., Washington, DC (US)

( * ) Notice: Subject to any disclaimer, the term of this patent is extended or adjusted under 35 U.S.C. 154(b) by 556 days.

(21) Appl. No.: 10/524,693

(22) PCT Filed: Aug. 18, 2003

(86) PCT No.: PCT/IB03/03698

§ 371 (c)(1),
(2), (4) Date: Feb. 15, 2005

(87) PCT Pub. No.: WO2004/017970

PCT Pub. Date: Mar. 4, 2004

(65) Prior Publication Data

US 2006/0025443 A1 Feb. 2, 2006

(30) Foreign Application Priority Data

Aug. 22, 2002 (GB) .................................. 0219639.2

(51) Int. Cl.
*A61K 31/451* (2006.01)
*C07D 211/88* (2006.01)
(52) U.S. Cl. ....................... 514/328; 546/219
(58) Field of Classification Search ................. 546/219; 514/328
See application file for complete search history.

(56) References Cited

U.S. PATENT DOCUMENTS 4,461,771 A * 7/1984 Gittos et al. ................. 514/328
4,835,151 A * 5/1989 Gittos ......................... 514/219

FOREIGN PATENT DOCUMENTS

GB 2 196 251 A 4/1988
GB 2 206 491 A 1/1989

OTHER PUBLICATIONS

RN 103353-87-3.*
Barga et al. "Making crystals from . . . " Chem. Commun. (2005) p. 3635-3645.*
Sheline et al. "Neuropsychopharmacology: the fifth generation of progress" p. 1065-1080 (2002).*
Tsuji et al. "Brain 5HT1A receptors . . . " Current Neuropharm. (2003) p. 315-324.*
Miner et al. "Chronic stress increases . . . " J. Neurosci. 26(5) p. 1571-1578 (2006).*
Berge et al. "Pharmaceutical salts" J. Pharm. Sci. 66(1) p. 1-19 (1977).*
Answers.com. "affective disorder" p. 1-8 (2007).*
Brittain "Polymorphism in pharmaceutical solids" p. 202 (1999).*
Evans "An introduction to crystal chemistry" p. 285-286 (1964).*
Holfels et al. "In vitro effects of . . . " Antimicr. Agents. Chemo. p. 1392-1396 (1994).*
Kaump et al. "Toxicity of the repository antimalarial . . . " CA64:14165 (1966).*

* cited by examiner

*Primary Examiner*—Celia Chang
(74) *Attorney, Agent, or Firm*—Bacon & Thomas, PLLC

(57) ABSTRACT

Novel pamoate salts of certain 3-phenyl-3-dimethylaminoalkyl-4,4-dimethylpiperidin-2,6-diones and pharmacologically acceptable solvates thereof are devoid of the weight loss and hepatocyte changes in the rat which limited to marginally effective levels the permitted clinical doses of the corresponding hydrochlorides in the treatment or prophylaxis of stress-related affective disorders such as anxiety, depression, migraine and sleep apnoea. The preferred pamoate salts are 3(3,5-dimethoxyphenyl)-3-(3-dimethylaminopropyl)-4,4-dimethylpiperidine-2,6-dione pamoate and, especially, 3(3-methoxyphenyl)-3-(3-dimethylaminopropyl)-4,4-dimethylpiperidine-2,6-dione pamoate.

1 Claim, No Drawings

PIPERIDIN-2,6-DIONE PAMOATE SALTS AND THEIR USE FOR THE TREATMENT OF STRESS-RELATED AFFECTIVE DISORDERS

CROSS-REFERENCE TO RELATED APPLICATIONS

This application is a 371 of PCT/IB2003/003698, filed 18 Aug. 2003, which claims priority from Great Britain Patent Application 0219639.2, filed 22 Aug. 2002.

TECHNICAL FIELD

The present invention relates to pamoate salts of certain 3-phenyl-3-dimethylaminoalkyl-4,4-dimethylpiperidin-2,6-diones and their use in the treatment of stress-related affective disorders. The term "stress-induced affective disorder" is used herein to include any disorder associated with elevated levels of 5-HT (5-hydroxytryptamine; serotonin) resultant from newly synthesised 5-HT.

BACKGROUND OF THE INVENTION

3-Phenyl-3-dimethylaminoalkyl-4,4-dimethylpiperidin-2,6-diones of the following Formula I and their acid addition salts have been known since 1974 (see BE-A-808,958; corresponding to GB-A-1,455,687 & U.S. Pat. No. 3,963,729):

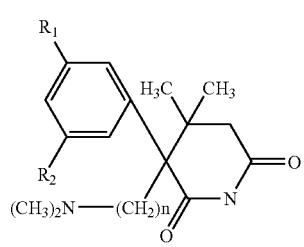

(I)

wherein:
$R_1$ represents methoxy, ethoxy or hydroxy;
$R_2$ represents methoxy, ethoxy, hydroxy or hydrogen; and
n represents 2 or 3.

They have been reported to have a range of pharmacological activities (see U.S. Pat. Nos. 3,963,729; 4,461,771; 4,738,973; 4,835,151; 4,835,151; 4,918,084; 4,994,475; 5,1177,086; GB-A-2,196,251 & GB-A-2,206,491) but were primary of interest for the treatment of stress-related affective disorders, especially anxiety and depression. They are the only compounds presently known to block selectively the activation of tryptophan hydroxylase induced by depolarisation, metabolic inhibitors, methyl xanthine, or stress. The compound of choice for clinical investigation was 3(3-methoxyphenyl)-3-(3-dimethylaminopropyl)-4,4-dimethylpiperidine-2,6-dione, which has been variously identified as AGN 2979 (which designation will be used in this application); BTG 1501; MDL 72415 and SC 48274. A large number of acid addition salts of AGN 2979 have been proposed but the hydrochloride has been the salt of choice because hydrochloride acid addition salts are the most commonly used acid addition salts and can be readily and inexpensively prepared and there was no reason to believe that any other salts would have any advantage over the hydrochloride. There has been no previous proposal or suggestion to use a pamoate salt of AGN 2979, or of any other base of Formula I or other 3-phenyl substituted-3-dialkylaminoalkyl-4,4-dialkylpiperidin-2,6-dione, for any purpose.

A number of papers relating to clinical trials of the hydrochloride salt of AGN 2979 have been conducted and the results published. These showed the salt to be effective in the treatment of anxiety and depression at about 4 mg/kg/day (200-400 mg/day for human patients). However, a 1-year sub-acute toxicity study of the hydrochloride (200 mg/kg/day p o. (i.e. by mouth)) in rats showed that the animals suffered an immediate and continuing weight loss (40% over the 1-year period) and, as revealed by post-mortem examination, hepatocyte changes which had not been detected by routine transaminase determinations during the year. As a result, the USA Food and Drugs Administration ("F.D.A") precluded the use of the dose levels previously used in the clinical trials. A subsequent clinical study by Cutler et al using an F.D.A. allowed dose of 1 mg b.i.d. (i.e. twice daily) (about 30 µg/kg/day) showed that the hydrochloride salt of AGN 2979 possessed only marginally effective anxiolytic properties at FDA permitted dose levels.

SUMMARY OF THE INVENTION

It has now surprisingly been found that the aforementioned problems of weight loss and hepatocyte changes can be overcome by the use of the pamoate salt instead of the hydrochloride, or other previously disclosed salt, of compounds of Formula I. These pamoate salts do not cause weight loss and the indications are that they will not cause hepatocyte changes over prolonged periods of treatment. Furthermore, it has been found that the pamoate salts of the compounds of Formula I, contrary to the known salts, are tasteless and allow the preparation of pharmaceutical compositions for the oral administration, especially in form of suspensions, syrups and the like. Thus, according to a first aspect of the present invention, there is provided the pamoate salts of 3-phenyl-3-dimethylaminoalkyl-4,4-dimethylpiperidin-2,6-diones of Formula I:

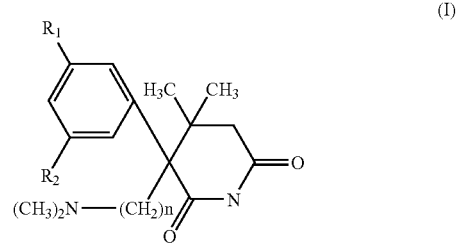

(I)

wherein:
$R_1$ represents methoxy, ethoxy or hydroxy;
$R_2$ represents methoxy, ethoxy, hydroxy or hydrogen; and
n represents 2 or 3,
and pharmacologically acceptable solvates thereof.

Pamoic acid is 4,4'-methylenebis[3-hydroxy-2-naphthalenecarboxylic acid] and is also known as embonic acid.

The compounds of Formula I exist in optical isomers and accordingly the pamoate salts can be used in racemate form or as individual (+) or (−) isomers. Presently the (−) isomer is preferred. The salts may exist in solvated, especially, hydrated, form and may hydrate on storage in a non-airtight environment.

In a second aspect, the present invention provides methods for the treatment or prophylaxis of stress-related affective disorders which comprise administering to a human or animal patient an effective amount of a pamoate salt of a compound of Formula I or a pharmacologically acceptable solvate thereof.

In a third aspect, the present invention provides pharmaceutical compositions comprising the pamoate salt of a compound of Formula I or a pharmacologically acceptable solvate thereof and a pharmacologically acceptable diluent or carrier.

In a fourth aspect, the present invention provides the pamoate salts of compounds of Formula I and pharmacologically acceptable solvates thereof for use in treatments of the human or animal body by therapy or diagnosis practised on the human or animal body.

In a fifth aspect, the present invention provides the use of pamoate salts of compounds of Formula I and pharmacologically acceptable solvates thereof in the manufacture of medicaments for the treatment or prophylaxis of stress-related affective disorders.

DETAILED DESCRIPTION

Examples of pamoate salts of compounds of Formula I include the following:

3-(3'-methoxyphenyl)-3-(2"-N,N-dimethylaminoethyl)-4,4-dimethylpiperidin-2,6-dione pamoate;

3-(3'-methoxyphenyl)-3-(3"-N,N-dimethylaminopropyl)-4,4-dimethylpiperidin-2,6-dione pamoate;

3-(3'-hydroxyphenyl)-3-(2"-N,N-dimethylaminoethyl)-4,4-dimethylpiperidin-2,6-dione pamoate;

3-(3'-hydroxyphenyl)-3-(3"-N,N-dimethylaminopropyl)-4,4-dimethylpiperidin-2,6-dione pamoate;

3-(3'-ethoxyphenyl)-3-(3"-N,N-dimethylaminopropyl)-4,4-dimethylpiperidin-2,6-dione pamoate;

3-(3',5'-dimethoxyphenyl)-3-(3"-N,N-dimethylaminopropyl)-4,4-dimethylpiperidin-2,6-dione pamoate;

3-(3',5'-dihydroxy)-3-(3"-N,N-dimethylaminopropyl)-4,4-dimethylpiperidin-2,6-dione pamoate; and 3-(3',5'-diethoxy)-3-(3"-N,N-dimethylaminopropyl)-4,4-dimethyl-piperidin-2,6-dione pamoate.

The preferred pamoate salts are those of compounds of Formula I in which $R_1$ represents methoxy and $R_2$ represents methoxy or hydrogen. The most preferred salts are 3(3,5-dimethoxyphenyl)-3-(3-dimethylaminopropyl)-4,4-dimethylpiperidine-2,6-dione pamoate and, especially, 3(3-methoxyphenyl)-3-(3-dimethylaminopropyl)-4,4-dimethylpiperidine-2,6-dione (AGN 2979) pamoate.

The pamoate salts of the invention can be prepared by conventional techniques for converting a free base into an acid addition salt or for converting one acid addition salt to another. For example, the pamoate salt is prepared by treating an ethanol solution of a compound of Formula I with a cooled solution of pamoic acid in ethanol; evaporation of the solvent under reduced pressure and recrystallisation of the residue from ethanol. Alternatively, a salt of a compound of Formula I may be converted into the pamoate by neutralisation, for example with ammonium hydroxide, and subsequent treatment with pamoic acid.

The compounds of Formula I can be prepared by the processes disclosed in U.S. Pat. No. 3,963,729 or U.S. Pat. No. 5,104,990, the disclosure of which documents are incorporated by this reference. The optical isomers can be separated in conventional manner, for example the (−) isomers can be separated by crystallisation of their (+) binaphthyl phosphoric acid salts from a suitable solvent such as ethanol.

The pamoate salts of the compounds of Formula I have the same qualitative pharmacological activity as that previously reported for the free base and other acid addition salts, especially the hydrochloride, and is especially useful for the treatment or prophylaxis of any stress-induced affective disorder. As mentioned above, the term "stress-induced affective disorder" is used herein to include any disorder associated with elevated levels of 5-HT (5-hydroxytryptamine; serotonin) resultant from newly synthesised 5-HT. In particular, the pamoate salts can be used to treat or prevent those neurological and psychological diseases and conditions in which newly synthesised 5-HT is implicated and for which antidepressant, anxiolytic and antipsychotic drugs are presently indicated. Non-limiting examples of such diseases or conditions are agoraphobia; anorexia nervosa; anxiety; anxiogenisis associated with withdrawal from drugs of abuse; bulimia nervosa; chronic paroxysmal hemicrania; depression (including prevention of depressive recurrences); diminution of the immune response associated with anxiety, depression or bereavement; disorders of sleep initiation or maintenance; disorders of the sleep-awake schedule; dream anxiety attacks; Huntington's chorea; Kleine-Levin syndrome; memory disturbance; Ménière's disease, menstrual-associated sleep syndrome; migraine; motion sickness; nausea incompletely relieved by $5HT_3$ antagonist administration, neurogenic pain; neuropathic pain; obsessive-compulsive disorder; panic attacks; posttraumatic stress disorder; pre-menstrual dysphoric disorder; recurrent brief depression; Restless Leg syndrome, schizophrenia; senile dementia; serotonin-irritation syndrome; sleep apnoea; sleep related cardiovascular symptoms; sleep related epileptic seizures; sleep-related cluster headaches; sleep-related myoclomus syndrome; social phobia; sudden infant death syndrome; and tinnitus.

The antidepressant action of AGN 2979 pamoate is believed to result from the inhibition of tryptophan hydroxylase activation, and the mechanism of this effect may involve blockade of K+ channels since other metabolic inhibitors, such as guanidine and sodium cyanide, which are known to open K+ channels, can activate tryptophan hydroxylase and this activation can be blocked by AGN 2979 pamoate.

The pamoate salts of the invention can be administered in any of the manners previously proposed for the hydrochloride salt. They can be administered alone or in the form of pharmaceutical preparations to the patient being treated either orally or parenterally, for example subcutaneously or intravenously. The amount of pamoate salt administered will vary and can be any effective amount. Depending upon the patient and the mode of administration, the quantity of pamoate salt administered may vary over a wide range to provide from about 0.1 mg/kg to about 20 mg/kg, usually about 0.5 mg/kg to about 10 mg/kg and preferably about 1 to about 5 mg/kg, of body weight of the patient per dose. Unit doses of these salts can contain, for example, from about 10 mg to about 500 mg, advantageously about 25 to about 200 mg. usually about 50 to about 100 mg of the pamoate salt and may be administered, for example, from 1 to 4 times daily. The term "unit dosage form" is used herein to mean a single or multiple dose form containing a quantity of the active ingredient in admixture with or otherwise in association with a diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

The pharmaceutical formulations in which form the pamoate salts of the invention will normally be utilised are prepared in a manner well known per se in the pharmaceutical art and usually comprise at least one active pamoate salt of the invention in admixture or otherwise in association with a pharmaceutically acceptable carrier or diluent therefor. For making those formulations, the active ingredient usually will be mixed with a carrier, or diluted by a diluent, or enclosed or encapsulated in a capsule, sachet, cachet, paper or other container. A carrier or diluent may be solid, semi-solid or liquid material that serves as a vehicle, excipient or medium for the active ingredient. Suitable carriers or diluents are well known per se. The formulations may be adapted for enteral or parenteral use and may be administered to the patient in the form of tablets, capsules, dragees, suppositories, syrups, suspensions or the like.

The invention is illustrated in the following non-limiting Examples.

EXAMPLE 1

Preparation of 3(3-methoxyphenyl)-3-(3-dimethylaminopropyl)-4,4-dimethyl-piperidine-2,6-dione pamoate (AGN 2979 pamoate)

(A) Preparation of diethyl 2-[2-cyano-5-(dimethylamino)-2-(3-methoxy-phenyl)-1,1-dimethylpentyl] propanedioate, monohydrochloride

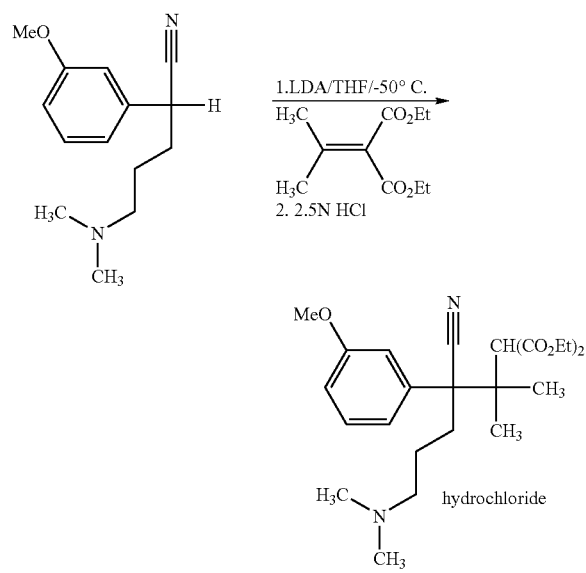

A nitrogen atmosphere was applied to a reaction vessel and 50 ml of dry tetrahydrofuran is added. The solvent was cooled to less than −40° C. and 32 mmoles of lithium diisopropylamide in tetrahydrofuranne-heptane was added (16 ml of a 2 M solution). A solution of 6.97 g (30 mmoles) of α-[3-(dimethylamino) propyl]-3-methoxybenzeneacetonitrile in 30 ml of tetrahydrofuran was added at less than −20° C. and left at this temperature for 30 min. The mixture was then cooled to −50° C. and a solution of 6.62 g (33 mmoles) of diethyl isopropylidenemalonate in 30 ml of tetrahydrofuran was added to the reaction mixture at a rate such that the temperature did not exceed −50° C. The mixture was stirred at −50° C. for 30 min and the cold reaction mixture added to a stirred solution of 30 ml of aqueous hydrochloric acid (36% w/w) in 100 ml of water cooled to 10° C. The mixture was extracted twice with toluene and the toluene phase is back extracted with a solution of 2 ml of hydrochloric acid (36% w/w) in 8 ml of water. The aqueous acidic extract was combined with the aqueous acidic phase from above and extracted twice with 50 ml portions of methylene chloride. The combined methylene chloride extracts were washed with water and the methylene chloride phase filtered and concentrated to low volume by distillation at atmospheric pressure. A 100 ml portion of ethyl acetate was added and the resulting slurry cooled to 5-10° C. The resulting solid was collected by filtration, washed with ethyl acetate and dried at 50° C. to give 10.1 g of white powder.

(B) Preparation of 3-(3-methoxyphenyl)-3-(3-dimethylaminopropyl]-4,4-dimethyl-piperidine-2,6-dione bisulphate salt (anhydrous)

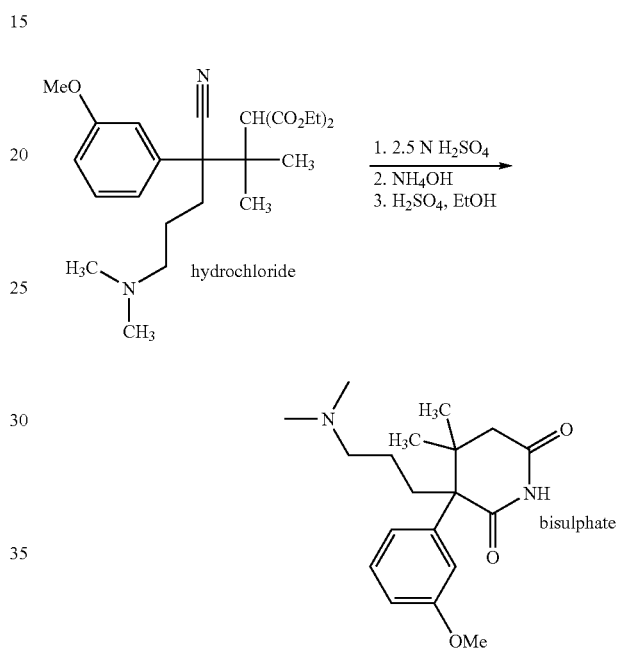

A 250 ml round-bottomed flask was charged with 10 g of the above-prepared diethyl 2-[2-cyano-5-(dimethylamino)-2-(3-methoxyphenyl)-1,1-dimethylpentyl]-propanedioate mono-hydrochloride, and a solution of 10.2 g of sulphuric acid (96% w/w) in 90 ml of water was added. The reaction mixture was refluxed for about 54 hours. When the reaction was complete (as indicated by thin layer chromatography) the solution was cooled to 25° C. The aqueous solution was washed with methylene chloride, the aqueous phase mixed with methylene chloride and basified with aqueous ammonium hydroxide (29% w/w) while maintaining the temperature at less than 30° C. After separation of the layers, the aqueous phase was extracted twice with methylene chloride, the combined organic phases concentrated and the residue crystallised in tert-butyl methyl ether to give 5.7 g of white powder. The crude compound was suspended in 200 ml of absolute ethyl alcohol, 1 equivalent of concentrated sulphuric acid added and the mixture is heated under reflux for 30 minutes to dissolve the salt. After cooling, most of the solvent was evaporated under reduced pressure and the residue was by crystallised means of a 50/50 mixture of diethylether-ethyl alcohol to give 6 g of white powder (melting point=159°-161° C.) and dried under reduced pressure.

(C) Preparation of 3-3-methoxyphenyl)-3-(3-dimethylaminopropyl]-4,4-dimethyl-piperidine-2,6-dione pamoate salt (anhydrous)

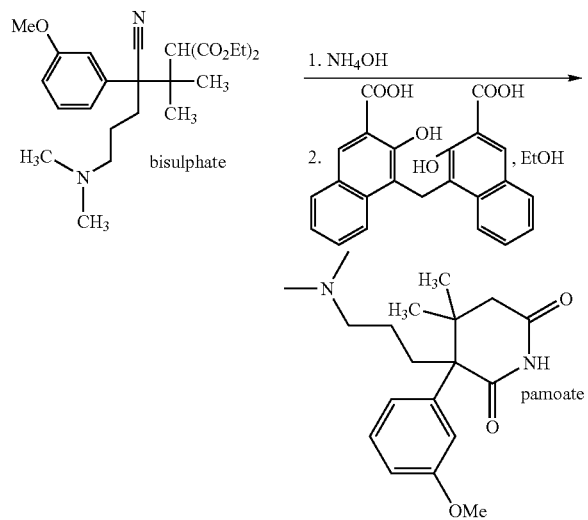

A solution of AGN-2979 bisulphate salt obtained in Step B (1 mmole, 430 mg) in 10 ml of water was mixed with methylene chloride (20 ml) and basified with aqueous ammonium hydroxide (29% w/w). After separation of the layers, the aqueous phase was extracted twice with methylene chloride. The combined organic phases were dried over anhydrous magnesium sulphate and the solvent was evaporated under reduced pressure. The residue was dissolved in ethanol (10 ml) and mixed with a hot solution of pamoic acid (embonic acid, 390 mg, 1 mmole) in hot ethanol (30 ml) and the mixture was heated to reflux. After cooling, the pamoate salt crystallised and the salt was recrystallised in hot ethanol to give a pale yellow powder (melting point=146°-150° C.

EXAMPLE 2

Tablets each having the following composition are prepared by conventional tabletting techniques:

| Ingredient | mg per tablet |
| --- | --- |
| (a) AGN 2979 pamoate | 50 |
| (b) Lactose | 51.5 |

-continued

| Ingredient | mg per tablet |
| --- | --- |
| (c) Maize starch dried | 45 |
| (d) magnesium stearate | 1.5 |

EXAMPLE 3

Suppositories are formed from the following composition:

| Ingredient | mg/suppository |
| --- | --- |
| (a) AGN 2979 pamoate | 20 |
| (b) Oil of Theobroma (cocoa butter) | 980 |

The compound (a) is powdered and passed through a BS No. 100 sieve (0.125 mm) and triturated with molten oil of Theobroma at 45° C. to form a smooth suspension. The mixture is well stirred and poured into moulds each of nominal 1 g capacity to produce suppositories.

EXAMPLE 4

Pills each having the following composition are prepared by blending the active (a) and the corn starch (b), then adding the liquid glucose (c) with thorough kneading to form a plastic mass from which the pills are cut and formed:

| Ingredient | per pill |
| --- | --- |
| (a) AGN 2979 pamoate | 50 mg |
| (b) Corn starch | 45 mg |
| (c) Liquid glucose | 7 cm$^3$ |

EXAMPLE 5

Gelatine capsules each containing 50 mg AGN 2979 pamoate and 20 mg talc are prepared by passing AGN 2979 and talc separately through a fine mesh screen, mixing the sieved powders and filling the mixed powder into hard gelatine capsules at a net fill of 70 mg per capsule.

The invention claimed is:
1. A pamoate salt of a 3-phenyl-3-dimethylaminoalkyl-4,4-dimethylpiperidin-2,6-dione, wherein the pamoate salt is 3(3-methoxyphenyl)-3-(3-dimethylaminopropyl)-4,4-dimethylpiperidine-2,6-dione pamoate.

* * * * *